United States Patent [19]

Riemann et al.

[11] Patent Number: 4,675,458

[45] Date of Patent: Jun. 23, 1987

[54] METHOD FOR MAKING 9,9-BIS-(4-HYDROXYPHENYL)-FLUORENE

[75] Inventors: Achim Riemann, Marburg; Werner Ude, Darmstadt, both of Fed. Rep. of Germany

[73] Assignee: Rönm GmbH, Darmstadt, Fed. Rep. of Germany

[21] Appl. No.: 783,463

[22] Filed: Oct. 3, 1985

[30] Foreign Application Priority Data

Oct. 27, 1984 [DE] Fed. Rep. of Germany ....... 3439484

[51] Int. Cl.$^4$ .............................................. C07C 39/12
[52] U.S. Cl. .................... 568/727; 568/719; 568/728
[58] Field of Search ................. 568/719, 727, 728

[56] References Cited

U.S. PATENT DOCUMENTS

| | | | |
|---|---|---|---|
| 2,775,620 | 12/1956 | Williamson | 568/728 |
| 3,821,317 | 6/1974 | Webb | 568/719 |
| 4,024,194 | 5/1977 | Corn | 568/719 |
| 4,049,721 | 9/1977 | Corn et al. | 568/719 |
| 4,467,122 | 8/1984 | Szabolcs | 568/727 |

FOREIGN PATENT DOCUMENTS 2948222  7/1981  Fed. Rep. of Germany ...... 568/719

OTHER PUBLICATIONS

Chem. Abstr. 95, 133593d (1981).
Schnell et al., Angew. Chem. Internat. Edit./vol. 2 (1963)/No. 7, pp. 373–379.
Schultz et al., Archiv der Pharmazie, 288 (1955) 234–246.

Primary Examiner—Werren B. Lone
Attorney, Agent, or Firm—Curtis, Morris & Safford

[57] ABSTRACT

A method for making 9,9-bis-(4-hydroxyphenyl)-fluorene by reacting fluorenone with phenol at a temperature from 20° to 100° C. in the presence of sulfuric acid of a concentration higher than 70 percent and of a mercaptan, and particularly beta-mercaptopropionic acid, as acidic condensing agents.

11 Claims, No Drawings

METHOD FOR MAKING 9,9-BIS-(4-HYDROXYPHENYL)-FLUORENE

The present invention relates to a method for making 9,9-bis-(4-hydroxyphenyl)-fluorene. More in particular, the invention relates to reacting fluorenone with phenol in the presence of an acidic condensing agent to produce the aforementioned compound.

A number of processes have been described in the art for the preparation of this compound, which is of interest as an intermediate product particularly in the manufacture of polycondensation products. However, these processes have considerable drawbacks in comparison with the process of the present invention. This condensation reaction is a special case of the synthesis of dihydroxydiarylmethane derivatives, which is accomplished by condensing carbonyl compounds with aromatic hydroxyl compounds in the presence of acidic condensing agents. Prior art acidic condensation catalysts include the hydrogen halides of fluorine, chlorine, or bromine, other halogen compounds such as phosgene, boron trifluoride, or aluminum chloride, as well as carboxylic acids, phosphoric acid, and also sulfuric acid.

According to the prior art, sulfuric acid employed as a condensing agent cannot be used as more than 70 percent acid since, according to H. Schnell and H. Krimm, Angew. Chemie 75 (1963) 663, concentrated sulfuric acid sulfonates both the aromatic hydroxyl starting compounds and the dihydroxydiarylmethane derivatives. It is further stated there that 70 percent sulfuric acid is less effective as a condensing agent than concentrated hydrochloric acid, and that the latter in turn is less effective than hydrogen chloride.

According to U.S. Pat. No. 4,049,721 and published German Patent Application DOS No. 29 48 222, only hydrogen chloride, introduced into the reaction mixture as a gas, has proved suitable up to now for use in the preparation of 9,9-bis-(4-hydroxyphenyl)-fluorene. In Example 1 of the U.S. patent cited, beta-mercaptopropionic acid is added as an effective co-catalyst to the hydrogen chloride, while divalent, trivalent, or tetravalent metal chlorides are added as supplemental condensing agents in the German patent application cited.

A serious drawback of working with hydrogen chloride or concentrated hydrochloric acid is that they are highly corrosive to the metal equipment used in the industrial-scale production of 9,9-bis-(4-hydroxyphenyl)-fluorene. The metal halides used as co-catalysts are just as corrosive.

The corrosiveness of reaction mixtures containing HCl is compounded by the fact that water is added during working up and the dilute aqueous solutions containing HCl so obtained are difficult to work up.

The object of the invention is to provide a method for making 9,9-bis-(4-hydroxyphenyl)-fluorene which eliminates the need for working with corrosive reaction mixtures containing chloride and which permits an unsulfonated product to be obtained in high purity and high yield.

It has been found that, surprisingly and contrary to the prevailing view, sulfuric acid can be used in concentrations even higher than 70 percent, and in fact in concentrations ranging from 75 to 100 percent, as a condensation catalyst in the reaction of fluorenone with phenol to give 9,9-bis-(4-hydroxyphenyl)-fluorene without sulfonation products being formed. The reaction proceeds rapidly to give a high yield of pure end product and the use of corrosive chloride-containing reaction mixture is avoided.

To increase the reaction rate further, mercaptans, and particularly mercaptocarboxylic acids, and advantageously beta-mercaptopropionic acid, are added as co-catalysts.

At temperatures above 100° C., sulfonated reaction products will form increasingly in addition to the desired 9,9-bis-(4-hydroxyphenyl)-fluorene. The resulting low yields of reaction product, which, moreover, are contaminated with byproducts that are difficult to separate, militates against operating at temperatures above 100° C. The lowest operating temperature is 20° C. At that temperature, the reaction still proceeds at a sufficiently fast rate and the reaction mixtures of the present invention are still in the liquid state. The preferred range is 20° C. to 70° C.

The reaction is advantageously carried out by stirring fluorenone and beta-mercaptopropionic acid at about 40° C. to 50° C. into molten phenol and metering concentrated sulfuric acid into this mixture in such a way that the temperature in the reaction vessel will not rise above 100° C. To keep the mixture stirrable, the phenol is advantageously used in an amount greater than the stoichiometric amount, that is, in an amount of up to about six moles of phenol per mole of fluorenone used.

To carry out the condensation reaction, sulfuric acid, employed as a condensation catalyst, is used in an amount from 0.1 to 5 moles, and preferably from 0.3 to 2 moles, of $H_2SO_4$ per mole of fluorenone. Sulfuric acid having a concentration of at least 75 percent, and particularly at least 80 percent, is employed. Concentrated (95 to 100%) sulfuric acid is preferred.

Mercaptans having 1 to 12 carbon atoms and possible further non-interfering functional groups such as hydroxyl and carboxyl groups can be used as co-catalysts. Such materials include ethyl mercaptan, n-butyl mercaptan, 1-octylmercaptan, tertiary dodecylmercaptan, mercaptoethanol, mercaptoacetic acid, and beta-mercaptopropionic acid. Preferably mercaptocarboxylic acids are used as co-catalysts. The mercaptans are used in an amount from about 0.002 to about 0.5, preferably from 0.004 to 0.2, mole of mercaptan per mole of fluorenone. In a preferred mode of operation, beta-mercaptopropionic acid is added in an amount of at least 0.005 mole per mole of fluorenone to be converted.

When these requirements are satisfied, the condensation will proceed rapidly. Long postreaction times are pointless since quantitative conversion of the fluorenone is obtained about one hour after completion of the addition of sulfuric acid.

To remove excess phenol, the sulfuric acid, and the co-catalyst, the reaction mixture is advantageously boiled repeatedly with water, optionally with the use of a water-miscible organic solvent such as methanol. The aqueous solution is separated each time and the product, then practically pure, is dried. Another effective method of removing excess phenol is by steam distillation.

A better understanding of the present invention and of its many advantages will be had by referring to the following specific Examples, given by way of illustration.

Example 1

45 g (0.25 mole) of fluorenone and 94 g (1 mole) of phenol were heated to 30° C. in a 250 ml four-neck flask with stirrer, dropping funnel, thermometer, and reflux condenser. 0.2 ml (2.3 millimoles) of beta-mercaptopropionic acid was added. The mixture was then cooled with iced water and 40 ml (0.72 mole) of 96 percent sulfuric acid was added dropwise in such a way that the temperature could be held within the range from 30° C. to 70° C. Thin-layer chromatographic analysis of the reaction mixture showed that the fluorenone had been completely converted after 15 minutes.

100 ml of methanol were then added and the solution was poured with stirring into 1 liter of cold water, whereupon a greasy mass separated with decolorization. The supernatant methanol/sulfuric acid solution was decanted and the residue was washed twice with 1 liter portions of water. After neutralization with aqueous ammonium carbonate solution, the excess phenol was removed by boiling three times with 1 liter portions of water. The particulate reaction product was filtered off by suction and dried at 60° C. in a vacuum oven.

Yield: 85.3 g (97.4 percent of theory). The product so obtained had a melting point of 222° C. After recrystallization from isopropyl alcohol, a product with a melting point of 223° C. (corresponding to that given in the literature) was obtained.

Examples 2 to 5

The same procedure and mixture were used as in Example 1, but the amount of sulfuric acid was varied. The results are presented in following Table 1.

TABLE 1

| Example | 96% Sulfuric acid | 100% Conversion after | Yield |
|---|---|---|---|
| 2 | 20 ml (0.36 mole) | 0.5 hr. | 85.0 g (97.0%) |
| 3 | 10 ml (0.18 mole) | 0.5 hr. | 84.2 g (96.1%) |
| 4 | 7.5 ml (0.13 mole) | 0.75 hr. | 85.5 g (97.6%) |
| 5 | 5 ml (0.09 mole) | No complete conversion after 5 hr. | |

EXAMPLE 6

45 g (0.25 mole) of fluorenone and 141 g (1.5 moles) of phenol were heated to 30° C. in a 500-ml four-neck flask equpped with stirrer, dropping funnel, thermometer, and reflux condenser, and 0.2 ml of beta-mercaptopropionic acid was added. The mixture was then cooled with ice water and 7.5 ml (0.13 mole) of 96% sulfuric acid was added dropwise in such a way that the temperature could be held within the range from 30° C. to 70° C. After 45 minutes, 150 ml of boiling water were added, followed by vigorous stirring. The resulting emulsion was then poured into 0.5 liter of cold water while the latter was being stirred. The supernatant solution was decanted and the residue was washed twice with 0.5 liter portions of cold water. Excess phenol was removed by boiling five times in 0.5 liter portions of water. Alternatively, the phenol could be separated by steam distillation.

Yield: 85.9 g (98.1% of theory).

EXAMPLES 7 to 9

The same procedure and mixture were used as in Example 6, but the amount of beta-mercaptopropionic acid was varied. The results are presented in following Table 2.

TABLE 2

| Example | beta-Mercaptopropionic acid | 100% Conversion after | Yield |
|---|---|---|---|
| 7 | 1.0 ml (11.5 millimoles) | 0.75 hr. | 85.5 g (97.6%) |
| 8 | 0.1 ml (1.2 millimoles) | No complete conversion after 5 hr. | |
| 9 | Without beta-mercaptopropionic acid | No complete conversion after 5 hr. | |

We claim:

1. A method for making 9,9-bis-(4-hydroxyphenyl)-fluorene which comprises reacting fluorenone with phenol in the presence of sulfuric acid having a concentration greater than 75 percent, as a condensing agent.

2. A method as in claim 1 wherein said sulfuric acid has a concentration of at least 80 percent.

3. A method as in claim 1 wherein said sulfuric acid has a concentration of at least 95 percent.

4. A method as in claim 1 wherein said sulfuric acid is used in an amount from 0.1 mole to 5 moles per mole of fluorenone.

5. A method as in claim 1 wherein said sulfuric acid is used in an amount from 0.3 mole to 2 moles per mole of fluorenone.

6. A method as in claim 1 wherein a mercaptan is additionally present as a co-condensing agent.

7. A method as in claim 5 wherein said mercaptan is a mercaptocarboxylic acid.

8. A method as in claim 5 wherein said mercaptan is beta-mercaptopropionic acid.

9. A method as in claim 5 wherein said mercaptan is present in an amount greater than 0.005 mole per mole of fluorenone to be converted.

10. A method as in claim 1 wherein the reaction is carried out at a temperature from 20° C. to 100° C.

11. A method as in claim 1 wherein the reaction is carried out at a temperature from 20° C. to 70° C.

* * * * *